United States Patent [19]

Kilpper et al.

[11] 4,233,459
[45] Nov. 11, 1980

[54] CONTINUOUS MANUFACTURE OF ANTHRANILIC ACID

[75] Inventors: Gerhard Kilpper, Battenberg; Johannes Grimmer, Ludwigshafen, both of Fed. Rep. of Germany

[73] Assignee: BASF Aktiengesellschaft, Fed. Rep. of Germany

[21] Appl. No.: 24,829

[22] Filed: Mar. 28, 1979

[30] Foreign Application Priority Data

Apr. 11, 1978 [DE] Fed. Rep. of Germany ....... 2815522

[51] Int. Cl.$^2$ ..................... C07C 99/00; C07C 99/12
[52] U.S. Cl. .................................................. 562/458
[58] Field of Search .................. 562/458, 433; 560/19

[56] References Cited

U.S. PATENT DOCUMENTS

| | | | |
|---|---|---|---|
| 3,322,820 | 5/1967 | Lehmann et al. | 562/458 |
| 3,847,974 | 11/1974 | Sturm et al. | 562/458 |
| 4,082,749 | 4/1978 | Juergen et al. | 562/458 |

OTHER PUBLICATIONS

Ullmanns Encyklopädie der technischen Chemie (4th edn.), vol. 8, p. 375.

*Primary Examiner*—Natalie Trousof
*Assistant Examiner*—James H. Reamer
*Attorney, Agent, or Firm*—Keil & Witherspoon

[57] ABSTRACT

Anthranilic acid is manufactured continuously by reacting an alkali metal phthalamate and/or phthalimidate with an alkali metal hypohalite in a reaction tube, the resulting anthranilic acid being treated, during or after the reaction, with reducing agents in two steps, the reducing agents employed in the two steps being different from one another, and an alkali metal dithionite or alkali metal formaldehyde-sulfoxylate being used as the reducing agent in the second treatment step. The product is a starting material for the preparation of dyes, crop protection agents and scents.

15 Claims, No Drawings

CONTINUOUS MANUFACTURE OF ANTHRANILIC ACID

The present invention relates to a process for the continuous manufacture of anthranilic acid by reacting an alkali metal phthalamate and/or phthalimidate with an alkali metal hypohalite in a reaction tube, the resulting anthranilic acid being treated, during or after the reaction, with reducing agents in two steps, the reducing agents employed in the two steps being different from one another, and an alkali metal dithionite or alkali metal formaldehyde-sulfoxylate being used as the reducing agent in the second treatment step.

German Pat. No. 1,224,748 discloses the continuous conversion of an alkali metal phthalamate to anthranilic acid by oxidation with an alkali metal hypochlorite. The starting materials, in the form of their cooled, aqueous solutions, are mixed with one another in a cooled mixing chamber and the first stage of the reaction, namely the formation of phenylisocyanate-2-carboxylic acid, is carried out in the part of a reaction column which contains a cooling system. In the second step, namely the formation of anthranilic acid, the reaction temperature is not allowed to exceed 70° C.

German published applications DAS Nos. 1,950,281 and 2,000,698 disclose a process for the continuous manufacture of anthranilic acid by reacting an alkali metal phthalamate and/or phthalimidate with a hypohalite in an aqueous medium, wherein (a) an aqueous solution of an alkali metal phthalamate and/or phthalimidate and an aqueous solution of an alkali metal hypochlorite are mixed in a mixing apparatus, (b) the resulting mixture is reacted in the first part of a narrow reaction tube, at a high flow rate, at from 10° to 50° C., under substantially adiabatic conditions, thereafter (c) the reaction of the mixture which leaves the first part of the reaction tube at a high flow rate is completed in the second part of the said tube at from 60° to 80° C. and (d) anthranilic acid is isolated in the conventional manner from the alkaline reaction mixture leaving the tube, and, if appropriate, a reducing agent is added during step (b) and/or step (c).

In this process, a part of the free alkali metal hydroxide is used whilst dissolving the starting material and a further part is added to the hypochlorite solution. Advantageously, aqueous solutions containing from 10 to 50 percent by weight of phthalimide and/or phthalamic acid and from 1 to 1.1 moles of alkali metal hydroxide per mole of phthalimide/phthalamic acid are employed. The above publication states that the aqueous hypohalite solution advantageously contains from 8 to 15 percent by weight of hypohalite and from 0 to 3, preferably from 0.02 to 2.1, moles of alkali metal hydroxide per mole of phthalimide/phthalamic acid. German published application DAS No. 2,000,698 expressly uses only one reducing agent, preferably sodium sulfite and sodium bisulfite (see also the Example); preferably, the reducing agent is added to the reaction mixture at one point only, advantageously directly after completion of the reaction in step (b).

German laid-open application DOS No. 2,328,757 describes a process for the preparation of amines, including anthranilic acid, by reacting a carboxylic acid amide with a hypochlorite in the presence of bromine, iodine and/or a haloamide and excess alkali metal hydroxide. It states that it is advantageous to employ aqueous suspensions containing from 1 to 50 percent by weight of the carboxylic acid amide starting material. The aqueous hypochlorite solutions in general contain from 5 to 15, preferably from 12 to 14, percent by weight of hypochlorite and can additionally contain from 0.2 to 2.5 moles, preferably from 1 to 2.1 moles, of alkali metal hydroxide per mole of hypochlorite. The starting mixture of the two starting materials in general contains a total of from 0.2 to 2.5 moles, preferably from 1 to 2.1 moles, of alkali metal hydroxide (not including the alkali contained in the hypochlorite) per mole of carboxylic acid amide group in the molecule of the carboxylic acid amide starting material. If the aqueous hypochlorite solution does not contain any free alkali metal hydroxide, it is advantageous to add from 0.2 to 2, preferably from 1 to 2, moles of alkali metal hydroxide per mole of hypochlorite at the start of, or during, the reaction.

A further process, described in German laid-open application DOS No. 2,357,749, relates to the similar preparation of amines by reaction of a carboxylic acid amide with a hypochlorite in the presence of excess alkali metal hydroxide and of polymerization inhibitors. Advantageously, an aqueous suspension containing from 1 to 50 percent by weight of the carboxylic acid amide starting material, an aqueous hypochlorite solution and the same amount of alkali metal hydroxide per mole of hypochlorite as in the process of German laid-open application No. 2,328,757 are employed. If the aqueous hypochlorite solution does not contain any free alkali metal hydroxide, it is again advantageous to add from 0.2 to 2, preferably from 1 to 2, moles of alkali metal hydroxide per mole of hypochlorite at the beginning, or during, the reaction.

For certain end uses, for example for the preparation of pharmaceutical products, it is necessary to employ anthranilic acid which will dissolve completely in dilute hydrochloric acid, giving a water-white solution, and which is at least 99 percent pure. The manufacture of anthranilic acid can result in intensely red or yellow compounds, which are adsorbed from the solution on precipitating the anthranilic acid and cause undesirable coloration when dissolved. Even though the process described in German published application DAS No. 2,000,698 allows the manufacture of relatively purer anthranilic acid, all the above processes are unsatisfactory in respect of the manufacture of particularly pure anthranilic acid. Additional purification processes, such as filtration in the presence of active charcoal, or re-precipitation, are technically complicated, are expensive and entail losses of end product.

We have found that anthranilic acid can be manufactured continuously in an advantageous manner by reacting an alkali metal phthalamate and/or phthalimidate with a hypohalite in an aqueous medium in a reaction tube, using an alkali metal dithionite and/or an alkali metal formaldehyde-sulfoxylate, if, during the reaction or after completion of the reaction 1. in a first step, the anthranilic acid obtained is treated with reducing agents different from the above alkali metal salts and
2. in a second step the treated anthranilic acid is treated with an alkali metal dithionite and/or an alkali metal formaldehyde-sulfoxylate.

Where sodium hydroxide and sodium hypochlorite are used, the reaction can be represented by the following equations:

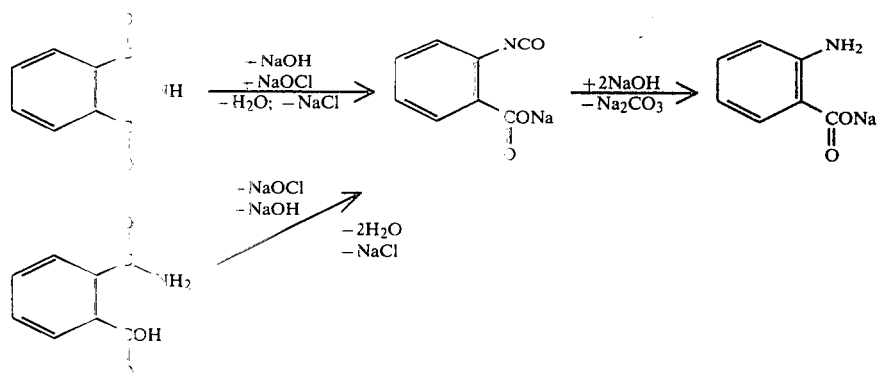

Compared to conventional processes, the process according to the invention gives anthranilic acid of greater purity, more simply and more economically, and with a better space-time yield of pure end product. The colored compounds present as impurities in the anthranilic acid are converted to a colorless, water-soluble form. The reaction according to the invention can also be carried out without loss of yield at from 80° to 100° C. in the step of the reaction in which the phenylisocyanate-2-carboxylic acid first formed is converted to anthranilic acid.

These advantageous results are furthermore achieved without the metering of the starting solutions having to be exceptionally uniform. Excess hypochlorite does not affect the results substantially. Fluctuations in the concentration of the adventitious materials ammonia (in the solution of the alkali metal phthalimidate or phthalamate) or sodium chlorate (in the hypochlorite solution) do not substantially affect the yield and purity (color) of the end product. Accordingly, the formation of sodium chlorate or other oxidizing by-products, which may arise in the first steps of the reaction, have no substantial effect on the amount or color of the anthranilic acid obtained. The process according to the invention, particularly on an industrial scale, gives anthranilic acid in good yield and in constantly higher purity than that achieved in the German published application DAS No. 2,000,698.

The reaction of the alkali metal phthalamate and/or phthalimidate with a hypohalite can be carried out continuously in a reaction tube in any desired manner, advantageously similar to the processes described in the above publications, especially the processes of German published application DAS No. 1,950,281 or German laid-open application DOS No. 2,328,757. In a particularly preferred embodiment of the reaction of the process according to the invention, (a) phthalimide and/or phthalamic acid is dissolved in an aqueous alkali metal hydroxide solution in a ratio of from 3 to 3.5 moles of alkali metal hydroxide per mole of phthalimide and/or of from 2 to 2.5 moles of alkali metal hydroxide per mole of phthalamic acid, (b) the resulting aqueous solution of alkali metal phthalamate and/or alkali metal phthalimidate and an aqueous solution of an alkali metal hypochlorite are mixed in a mixing apparatus, (c) the resulting mixture is reacted, in the first part of a reaction tube, at from 10° to 54° C. under substantially adiabatic conditions and at a high flow rate, thereafter (d) the reaction of the mixture leaving the first part of the reaction tube at a high flow rate is completed in the second part of the said tube at from 55° to 90° C. and (e) anthranilic acid is isolated in the conventional manner from the alkaline reaction mixture which leaves the tube.

Preferably, the reaction is carried out in the presence of bromine, iodine and/or an amide of the formula $$X-\underset{\underset{R^2}{|}}{N}-R^1 \qquad I$$

where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, together with the adjacent nitrogen, be members of a heterocyclic radical which contains one or more sulfonyl groups, or phosphonyl groups of the formula

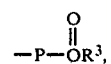

where $R^3$ is hydrogen or an alkali metal, adjacent to the nitrogen, and $R^1$ and $R^2$ together may also be

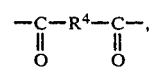

where $R^4$ is alkylene

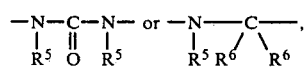

$R^5$ is hydrogen, chlorine or bromine and $R^6$ is an aliphatic radical.

The starting materials used can be an alkali metal phthalamate and/or phthalimidate and a hypohalite in an aqueous medium, as a rule in the form of the aqueous alkaline solutions of these reactants. Advantageously, an aqueous solution containing from 10 to 50 percent by weight of phthalimide and/or phthalamic acid and from 1 to 1.1 moles of alkali metal hydroxide per mole of phthalimide/phthalamic acid is employed. Sodium hydroxide and potassium hydroxide are the preferred alkali metal hydroxides.

The aqueous hypohalite solution advantageously contains from 5 to 15, preferably from 12 to 14, percent by weight of hypohalite and may in addition contain from 0.2 to 2.5 moles, preferably from 1 to 2.1 moles, of alkali metal hydroxide per mole of hypohalite. In general, the starting mixture of the two materials contains a total of from 0.9 to 1.5, preferably from 0.95 to 1.1, moles of hypohalite and, advantageously, a total of from 0.2 to 2.5 moles, preferably from 1 to 2.1 moles, of alkali metal hydroxide (not counting the alkali contained in the hypohalite) per mole of phthalimide and/or phthalamic acid. If the aqueous hypohalite solution does not contain any free alkali metal hydroxide, it is advantageous to introduce from 0.2 to 2, preferably from 1 to 2, moles of alkali metal hydroxide per mole of hypohalite at the beginning of, or during, the reaction. Preferred hypohalites are hypochlorites, especially alkali metal hypochlorites, for example the sodium or potassium salt, or alkaline earth metal hypochlorites, for example the calcium salt.

In the above particularly preferred embodiment, the starting material is dissolved, in step (a), in an aqueous alkali metal hydroxide solution, advantageously potassium hydroxide solution and especially sodium hydroxide solution. Preferred aqueous solutions contain from 10 to 50, more especially from 15 to 30, percent by weight (based on the amount of pure water) of phthalimide and/or of phthalamic acid and from 3 to 3.5, preferably from 3.1 to 3.2, moles of alkali metal hydroxide per mole of phthalimide and/or from 2 to 2.5, preferably from 2.1 to 2.2, moles of alkali metal hydroxide per mole of phthalamic acid. The process of solution is advantageously carried out continuously at from $-5°$ to $+50°$ C., preferably from $20°$ to $30°$ C., under atmospheric or superatmospheric pressure. If a catalyst, for example one of those described in German laid-open application DOS No. 2,357,749 or, advantageously, one of those described in German laid-open application DOS No. 2,328,757, is used, it is advantageously added to the starting material, or to its solution, as early as step (a). However, the catalyst, advantageously as a mixture with water, can also be added to the starting mixture separately or together with the hypohalite.

Advantageous catalysts are bromide, iodine and/or the above amides I, in general in an amount of from 0.0001 to 0.1, preferably from 0.001 to 0.01, mole of catalyst per mole of phthalimide or phthalamic acid. Instead of the said materials, compounds which form such materials under the reaction conditions can also be used, for example bromides and iodides instead of bromine or iodine. Advantageously, a water-soluble halide is used. These may advantageously be the alkaline earth metal halides and especially the alkali metal halides, for example calcium bromide, calcium iodide, magnesium bromide, magnesium iodide, lithium bromide, lithium iodide and especially sodium and potassium bromide and iodide. Preferred amides I are those where $R^1$ is a sulfonic acid group, a sulfonate radical, especially an alkali metal sulfonate radical, such as the sodium sulfonate or potassium sulfonate radical or a sulfonamide group, $R^2$ is chlorine, bromine, alkyl of 1 to 4 carbon atoms or, in particular, hydrogen, X is bromine, chlorine or, advantageously, hydrogen, $R^1$ and $R^2$ may also, together with the adjacent nitrogen, be members of a heterocyclic 5-membered or 6-membered ring which contains one or more sulfone groups or phosphonyl groups of the formula

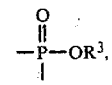

where $R^3$ is hydrogen or an alkali metal, especially sodium or potassium, adjacent to the nitrogen, and $R^1$ and $R^2$ together are

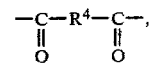

where $R^4$ is alkylene of 2 to 4 carbon atoms,

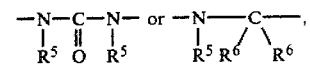

$R^5$ is hydrogen, chlorine or bromine and $R^6$ is alkyl of 1 to 4 carbon atoms, especially methyl. A phenyl nucleus may be fused to the above heterocyclic ring. Advantageously, the heterocyclic radical contains 2 sulfone or phosphone groups adjacent to the nitrogen or two or three sulfonamido groups or phosphonamido groups, in particular in the same ring where polynuclear heterocyclic radicals are concerned. The above preferred radicals may in addition be substituted by groups or atoms which are inert under the reaction conditions, for example chlorine, bromine or alkyl of 1 to 4 carbon atoms, or by carboxyl or carboxylate groups present as phenyl substituents.

Examples of suitable catalysts are glutarimide, adipimide and succinimide and, preferably, cyanuric acid, 5,5-dimethylhydantoin, trisulfamide, N-methyl-sulfamic acid and sodium triimidometaphosphate, as well as appropriate mixtures of the above haloamides I; particularly preferred catalysts are sulfamic acid and its salts, advantageously alkali metal salts, such as the sodium salt or potassium salt, and especially sulfamide, which may or may not be mixed with the above amides I.

The aqueous hypohalite solutions from stage (b) of the above particularly preferred embodiment advantageously contain from 5 to 15, especially from 12 to 14, percent by weight of hypohalite and no substantial amounts, or at most up to 0.01 mole, of excess alkali metal hydroxide per mole of phthalimide/phthalamic acid. Preferred alkali metal hypohalites are alkali metal hypochlorites, especially the potassium or sodium salt. In general, the reaction is carried out with a ratio of from 1 to 2, preferably from 1 to 1.2, moles of hypohalite per mole of phthalimide and/or phthalamic acid. Advantageously, the starting material, in the form of its aqueous alkaline solution, of the above concentration, as obtained from stage (a), is mixed with the alkali metal hypochlorite solution in stage (b) in the above ratio in a mixing device. Such devices may be mixing cells, mixing nozzles or chambers fitted with high-speed stirrers. Mixing is as a rule carried out continuously, at from $0°$ to $50°$ C., advantageously from $25°$ to $45°$ C., under atmospheric or superatmospheric pressure.

The starting materials can, in general terms, be reacted in the reaction tube at from $0°$ C. to $100°$ C., preferably from $10°$ C. to $85°$ C., under atmospheric or superatmospheric pressure, continuously or batchwise.

The reaction may be carried out by keeping a mixture of the starting materials, catalyst, alkali and water at the reaction temperature for from 1 to 4,000 seconds. In a further embodiment, which at the same time illustrates the particularly simple and advantageous manner in which an installation employing the process of the invention may be operated, the carboxylic acid amide starting material, eg. phthalamic acid, is first prepared from the carboxylic acid anhydride and ammonia, with or without alkali metal hydroxide, at, as a rule, from 20° to 80° C., and the reaction mixture thus formed is employed directly, without isolating the product, as the starting material for the process according to the invention. The reaction can also advantageously be carried out in accordance with the above steps (a) to (d) of the process of German published application DAS No. 1,950,281.

In the above, particularly preferred embodiment, the reaction is advantageously carried out in 2 reaction chambers (stages (c) and (d)), under conditions which substantially avoid re-mixing in the two chambers, and under substantially adiabatic conditions in the first stage. The reaction takes place in 2 steps, namely step (c), in which the starting material is converted, via the alkali metal N-chlorophthalamate to the alkali metal phenylisocyanate-2-carboxylate and the subsequent stage (d), wherein this alkali metal salt is converted to anthranilic acid. The first reaction stage is carried out under substantially adiabatic conditions, under which the heat of reaction as a rule raises the reaction mixture to 20°–50° C. From the mixing device, the reaction mixture passes into the reaction chamber to the first reaction stage (stage (c)) which consists of a reaction tube, which is advantageously narrow, and from there, after reaction has taken place, the mixture passes into the reaction chamber of the next stage (stage (d)). The mixing apparatus, the reaction chamber in which the first stage takes place, and the solutions of the starting materials do not require cooling. An advantageous feature of the process in the above particularly preferred embodiment is that re-mixing in stage (c) is substantially avoided, and that the reaction mixture is rapidly removed from (c) and fed to stage (d) under conditions which substantially avoid re-mixing. Advantageously, a high flow rate of the reaction mixture is achieved by selecting a narrow cross-section of the reaction tube in the first stages and by using appropriate conveying pumps. Examples of suitable pumps are jet pumps, rotary pumps, rotary piston pumps, Roots pumps, screw piston pumps, eccentric pumps, vane pumps, centrifugal pumps, axial flow pumps and propeller pumps. In a preferred embodiment of the process, the flow rate is determined by the cross-section and length of the reaction tube. For example, reactor cross-sections of from 10 to 10,000 mm$^2$ and flow rates of from 0.1 to 10, especially from 0.2 to 3, and preferably from 0.5 to 1.2, m/sec are advantageous. At these flow rates, the starting material is substantially converted, in stage (c), via N-chloro-phthalamic acid to the alkali metal phenylisocyanate-2-carboxylate in a residence time of, as a rule, from 0.4 to 40, preferably from 0.6 to 20 seconds. As a result of the high flow rate, the alkali metal salt formed is immediately removed from the reaction chamber of stage (c) and fed to the next stage where it is converted to anthranilic acid, in general in a residence time of from 0.3 to 150 seconds, preferably from 0.3 to 40 seconds. The high flow rate at the same time substantially prevents re-mixing throughout the entire reaction of the mixture. In particular, re-mixing of the end product with the reaction mixture of stage (c) is avoided and hence the formation of by-products by reaction of the hypohalite or of the N-chloro-phthalamic acid with the end product and/or by similar reactions in the mixtures of stages (c) and (d) is suppressed. The reaction is carried out at from 10° to 54° C., preferably from 20° to 54° C., especially from 30° to 54° C., in stage (c) and at from 55° to 90° C., preferably from 60° to 90° C., in stage (d), under atmospheric or superatmospheric pressure. The completion of reaction stage (c) is as a rule shown by a temperature rise from 20°–30° C. to about 42°–53° C. The cross-section, flow rate and temperature of the starting solutions in general decide the length of the tube zone in which the first reaction stage (c) is carried out. For example, with a tube cross-section of 2,200 mm$^2$, a flow rate of about 1 m/sec and a starting temperature of about 40° C., stage (c) is frequently complete after a length of about 1.5 meters of the reaction tube has been traversed. At the end of the complete reaction sequence, the reaction mixture is taken off. The end products may be isolated from the alkaline solution by precipitation with an acid, e.g. hydrochloric acid or sulfuric acid, followed by filtration.

The process according to the invention is based on the observation that it is not reducing agents in general which improve the purity of the end product, and that instead a treatment with two different reducing agents is necessary to achieve optimum yields of very pure end product; it is a critical characteristic of the invention that in the first step a substantial number of reducing agents, but under no circumstances an alkali metal dithionite and/or alkali metal formaldehyde-sulfoxylate, may be employed, whilst in the second step it is only an alkali metal dithionite and/or alkali metal formaldehyde-sulfoxylate which can be used. The advantageous results which this specific sequence of selective reducing agents produces in the process according to the invention are surprising.

In the first treatment step a substantial number of reducing agents which are soluble in, or miscible with, water and/or alkalis can be used. Examples of suitable reducing agents are hydrides, e.g. sodium borohydride and lithium triethoxy-aluminum hydride; reducing sulfur compounds, e.g. sodium sulfide, sodium bisulfide, ammonium sulfide, sulfurous acid, sulfur dioxide, sodium thiosulfate and thiourea dioxide; hydrazine and its salts, eg. the sulfate or chloride, and glucose. Preferred reducing agents are sodium sulfite and sodium bisulfite. The reducing agent may be used in the stoichiometric ratio or in an excess over the hypohalite employed, this excess preferably being from 0.0005 to 0.2, especially from 0.005 to 0.1, equivalent per mole of hypohalite employed. It is advantageous to use solutions of the reducing agent in water, e.g. aqueous sodium bisulfite solutions of from 10 to 40 percent strength by weight.

The alkali metal dithionite and/or alkali metal formaldehyde-sulfoxylate can be used in the stoichiometric ratio or in an excess over the hypohalite employed, preferably an excess of from 0.0005 to 0.2, especially from 0.005 to 0.1, equivalent of alkali metal dithionite and/or alkali metal formaldehyde-sulfoxylate per mole of hypochlorite employed. Advantageously, aqueous solutions of the reducing agent, for example aqueous sodium dithionite solutions of from 1 to 20 percent strength by weight, are used. A ratio of from 0.1 to 1, especially from 0.2 to 0.8, equivalent of alkali metal dithionite and/or alkali metal formaldehyde-sulfoxylate per mole of reducing agent used in the first treatment step is advantageous. Amongst the alkali metal dithionites, sodium dithionite is preferred, whilst amongst the alkali metal formaldehyde-sulfoxylates sodium formaldehyde-sulfoxylate is preferred. Sodium dithionite can also be used in the form of hydrosulfite, and sodium formaldehyde-sulfoxylate (sodium hydroxymethanesulfinate) can also be used in the form of the commercial product Rongalite (a registered tradename).

In both steps, the treatment is as a rule carried out at from 0° to +100° C., preferably at from 5° to 90° C., in particular at from 55° to 90° C. in the first step and from 88° to 5° C. in the second step, batchwise or, advantageously, continuously, under atmospheric or superatmospheric pressure. Both steps can be carried out during the reaction, the first step for example after the start or during the first half of the reaction time and the second step in the second half or at the end of the second half of the reaction time; in that case, as described above, the first step is advantageously stage (b) of German published application DAS No. 1,950,281 or, in the above preferred embodiment, stage (c) thereof, and the second step is stage (c) of the process of the said DAS or, in the above preferred embodiment, stage (d) thereof. Advantageously, however, both treatment steps are carried out during the reaction and in the second half of the reaction time; for example, the first treatment step is carried out at the beginning of, or during, the second half of the reaction time or at the beginning of, or during, stage (c) of the process of German published application DAS No. 1,950,281, or, in the above preferred embodiment, at the beginning of, or during, stage (d) of the said DAS, whilst the second treatment step is carried out shortly before the end, or at the end, of the second half of the reaction time, ie. shortly before the end, or at the end, of stage (c) of the process of German published application DAS No. 1,950,281, or, in the above preferred embodiment, shortly before the end, or at the end, of stage (d) of the said DAS. Both treatment steps can also advantageously be carried out after the reaction, for example the first treatment step directly after completion of the reaction or of stage (c) of the process of German published application DAS No. 1,950,281 or of stage (d) in the above preferred embodiment, after which the second treatment step is carried out and finally the isolation of the end product is commenced by acidifying the treated mixture. The following embodiment is particularly preferred: the first treatment step commences shortly before the end, or at the end, of the reaction, i.e. of stage (c) of the process of German published application DAS No. 1,950,281 or of stage (d) in the above preferred embodiment, advantageously from 0.2 to 0 second before the end point of the reaction, and, after addition of the reducing agent, is advantageously continued to provide a residence time of the reaction mixture in the presence of the reducing agent of from 0.2 to 40, especially from 1 to 15, seconds, taken from the beginning of the addition of the reducing agent. Thereafter, the second treatment step and the addition of alkali metal dithionite and/or alkali metal formaldehyde-sulfoxylate is advantageously started, allowing a residence time of from 0.2 to 120, especially from 0.5 to 60, seconds from the start of the addition of alkali metal dithionite and/or alkali metal formaldehyde-sulfoxylate. It is also possible, in both steps, to add the reducing agent, or the alkali metal dithionite and/or alkali metal formaldehyde-sulfoxylate, slowly during the above residence time; however, more rapid addition, subsequently allowing a residence time during which no more is added, is more advantageous. The first treatment step is advantageously carried out whilst the reaction mixture is still at the temperature which it has before or at the end of the reaction, ie. the above temperature of stage (c) of the process of German published application DAS No. 1,950,281 or of stage (d) in the above preferred embodiment. In the second treatment step, the reaction mixture is then advantageously kept at this temperature for a further short period, for example from 0.2 to 40 seconds, after which it is cooled, advantageously to 5°–25° C. The rate of addition in both treatment steps depends as a rule on the flow rate of the reaction mixture, and must take into account the concentration of the solution added and the above ratio of reducing agent to hypohalite starting material. The reducing solution may be metered in by any desired method, for example through chambers equipped with mixers, through mixing nozzles or preferably through a mixing cell. After addition of the reducing agent, the treatment can take place in the reaction tube at a high flow rate, for example from 0.2 to 3 m/sec, or, without loss of yield, in a reaction tube of any desired other size; the further treatment, in both steps, can advantageously also be carried out in an extension of the reaction tube or, continuously, in downstream separate tubular reactors provided for the treatment. Advantageously, both the first and second steps of the treatment are carried out at a pH of from 9 to 14.

After the treatment steps, the end product is advantageously isolated in the conventional manner, for example by bringing the pH to 4.2 and filtering off the anthranilic acid or extracting it with an organic solvent, e.g. benzene or a chlorohydrocarbon, such as trichloroethylene.

The compound obtainable by the process of the invention is a valuable starting material for the preparation of dyes, crop protection agents and scents. Regarding its use, reference may be made to the patents mentioned above and to Ullmanns Encyklopädie der technischen Chemie (4th edition), volume 8, page 375.

In the Examples which follow, parts are by weight and bear the same relation to parts by volume as that of the kilogram to the liter.

EXAMPLE 1

An installation comprising a mixing nozzle and a reaction tube having a reaction chamber of 1.1 meters length and 53 millimeters internal diameter is used. Per hour, 590 parts of liquid phthalimide are continuously dissolved, in a mixing nozzle, in 2,103 parts of aqueous 25 percent strength by weight sodium hydroxide solution and 4,752 parts of water, and 18 parts of a 30 percent strength by weight aqueous solution of the sodium salt of sulfamic acid are introduced. The solution formed is mixed, in the mixing nozzle, with 2,100 parts per hour of aqueous sodium hypochlorite solution (representing 290 parts per hour of sodium hypochlorite; 13.8 percent by weight of active chlorine) at 42° C. The flow rate in the downstream part of the reaction tube is 1.1 meters per second, with a residence time of one second. In the first part of the reaction chamber (stage (c)) (0.3 m length) the reaction mixture is reacted substantially adiabatically (at from 42° to 53° C.), whilst in the remainder of the reaction chamber (stage (d)) its temperature rises autogenously to 89° C. 25 parts per hour of 40 percent strength by weight aqueous sodium bisulfite solution are added continuously to the mixture at a distance of 0.90 meter from the inlet of the reaction tube (representing the start of stage (c)). The mixture remains in the reaction tube at 89° C., at the same flow rate, for 10 seconds after the addition, 15 parts per hour of 20 percent strength aqueous sodium dithionite solution are then added. The solution is cooled to 10° C. and brought to pH 4.2 with hydrochloric acid, the product is filtered off and the filter residue is washed with water and dried. The residence time of the second treatment step (from the beginning of the addition of the dithionite to the addition of the acid) is 40 seconds, and the residence time from when cooling starts is 30 seconds. Per hour, 535 parts (97% of theory) of 99.9% pure anthranilic acid of melting point 146.1° C. are obtained; space-time yield: 268 parts per hour per liter.

EXAMPLE 2

The reaction is carried out as described in Example 1, but with addition of 40 parts per hour of sodium formaldehyde-sulfoxylate instead of sodium dithionite. Anthranilic acid is obtained in the same yield and purity.

EXAMPLE 3 (COMPARISON)

(a) If the reaction is carried out as described in Example 1, but with the addition of 25 parts per hour of 40 percent strength by weight aqueous sodium bisulfite solution instead of sodium dithionite in the second treatment step, 530 parts per hour (96% of theory) of 98.9 percent pure anthranilic acid, of melting point 145.7° C., are obtained. Space-time yield: 265 parts per hour per liter.

(b) If the reaction is carried out as described in Example 1, but with the addition of 15 parts per hour of 20 percent strength by weight aqueous sodium dithionite solution, instead of sodium bisulfite, in the first treatment step and with the addition of 25 parts per hour of 40 percent strength by weight aqueous sodium bisulfite solution, instead of sodium dithionite, in the second treatment step, 525 parts per hour (95% of theory) of 99 percent pure anthranilic acid, of melting point 145.9° C., are obtained. Space-time yield: 263 parts per hour per liter.

(c) If the reaction is carried out as described in Example 1, but with the addition of 15 parts per hour of 20 percent strength by weight aqueous sodium dithionite solution in the first treatment step and with the addition of 15 parts per hour of 20 percent strength by weight aqueous sodium dithionite solution in the second treatment step, 530 parts per hour (96% of theory) of 98.9 percent pure anthranilic acid, of melting point 145.9° C., are obtained. Space-time yield: 265 parts per hour per liter.

(d) The anthranilic acid obtained according to Example 3(a)–(c) has a brownish hue and contains insoluble matter, as shown by a solution in dilute hydrochloric acid. Extinction measurements carried out on a 5 percent strength by weight solution of anthranilic acid in 1 N hydrochloric acid at a wavelength of 430 nanometers give the following values:

| Example | Extinction |
|---------|------------|
| 1 | 0.1 |
| a) | 0.2 |
| b) | 0.2 |
| 3(c) | 0.2 |

We claim:

1. A process for the continuous manufacture of anthranilic acid by reacting an alkali metal phthalamate, phthalimidate, or a mixture thereof, with a hypohalite in an aqueous medium in a reaction tube, wherein, during the reaction forming the anthranilic acid or after completion of the reaction, (1) in a first step, the anthranilic acid so obtained is treated with reducing agents which are not alkali metal dithionite or alkali metal formaldehyde-sulfoxylates and (2) in a second step the treated anthranilic acid is then further treated with an alkali metal dithionite, an alkali metal formaldehyde-sulfoxylate or a mixture thereof.

2. A process as claimed in claim 1, wherein (a) phthalimide and/or phthalamic acid is dissolved in an aqueous alkali metal hydroxide solution in a ratio of from 3 to 3.5 moles of alkali metal hydroxide per mole of phthalimide and/or of from 2 to 2.5 moles of alkali metal hydroxide per mole of phthalamic acid, (b) the resulting aqueous solution of alkali metal phthalamate and/or alkali metal phthalimidate and an aqueous solution of an alkali metal hypochlorite are mixed in a mixing apparatus, (c) the resulting mixture is reacted, in the first part of a reaction tube, at from 10° to 54° C. under substantially adiabatic conditions and at a high flow rate, thereafter (d) the reaction of the mixture leaving the first part of the reaction tube at a high flow rate is completed in the second part of the said tube at from 55° to 90° C. and (e) anthranilic acid is isolated in the conventional manner from the alkaline reaction mixture which leaves the tube.

3. A process as claimed in claim 1, wherein the reaction is carried out in the additional presence of bromine, iodine and/or a haloamide of the formula

where $R^1$ is a sulfonic acid group, a sulfonate radical or a sulfonamide group, $R^2$ is hydrogen, an aliphatic radical, chlorine or bromine, X is chlorine, bromine or hydrogen, $R^1$ and $R^2$ may also, together with the adjacent nitrogen, be members of a heterocyclic radical which contains one or more sulfonyl groups, or phosphonyl groups of the formula

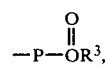

where $R^3$ is hydrogen or an alkali metal, adjacent to the nitrogen, and $R^1$ and $R^2$ together may also be

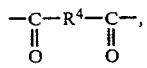

where $R^4$ is alkylene,

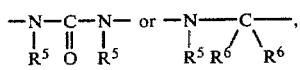

$R^5$ is hydrogen, chlorine or bromine and $R^6$ is an aliphatic radical.

4. A process as claimed in claim 1, wherein an aqueous hypohalite solution of from 5 to 15 percent strength by weight is used.

5. A process as claimed in claim 1, wherein the reaction is carried out with a total of from 0.9 to 1.5 moles of hypohalite and a total of from 0.2 to 2.5 moles of alkali metal hydroxide (not counting the alkali contained in the hypohalite) per mole of phthalimide and/or phthalamic acid.

6. A process as claimed in claim 1, wherein the reaction is carried out with an aqueous solution containing from 10 to 50 percent by weight (based on the amount of pure water) of phthalimide and/or phthalamic acid, which solution contains from 3 to 3.5 moles of alkali metal hydroxide per mole of phthalimide and/or from 2 to 2.5 moles of alkali metal hydroxide per mole of phthalamic acid.

7. A process as claimed in claim 1, wherein the reaction is carried out with bromine, iodine and/or a haloamide, using from 0.0001 to 0.1 mole of these catalysts per mole of phthalimide or phthalamic acid.

8. A process as claimed in claim 1, wherein the starting materials are reacted continuously in a reaction tube at from 0° C. to 100° C.

9. A process as claimed in claim 2, wherein, allowing a residence time of from 0.4 to 40 seconds, the starting material is substantially converted, in stage (c), via the N-chloro-phthalamic acid to the alkali metal phenylisocyanate-2-carboxylate and the latter is immediately withdrawn from the reaction chamber of stage (c) and fed to the following stage, where it is converted, with a residence time of from 0.3 to 150 seconds, to anthranilic acid.

10. A process as claimed in claim 2, wherein stage (c) is carried out at from 10° to 54° C. and stage (d) at from 55° to 90° C.

11. A process as claimed in claim 1, wherein the reaction is carried out with from 0.0005 to 0.2 equivalent of reducing agent per mole of hypohalite employed.

12. A process as claimed in claim 1, wherein the reaction is carried out with from 0.0005 to 0.2 equivalent of alkali metal dithionite and/or alkali metal formaldehyde-sulfoxylate per mole of hypohalite employed.

13. A process as claimed in claim 1, wherein the reaction is carried out with from 0.1 to 1 equivalent of alkali metal dithionite and/or alkali metal formaldehyde-sulfoxylate per mole of reducing agent used in the first treatment step.

14. A process as claimed in claim 1, wherein the treatment is carried out at from 10° to 90° C. in both steps.

15. A process as claimed in claim 1, wherein the treatment is carried out continuously, at from 55° to 90° C. in the first step and at from 88° to 5° C. in the second step.

* * * * *